United States Patent [19]

Freitag

[11] Patent Number: 5,674,277
[45] Date of Patent: Oct. 7, 1997

[54] STENT FOR PLACEMENT IN A BODY TUBE

[75] Inventor: Lutz Freitag, Hemer, Germany

[73] Assignee: Willy Rüsch AG, Kernen, Germany

[21] Appl. No.: 561,811

[22] Filed: Nov. 22, 1995

[30]      Foreign Application Priority Data

Dec. 23, 1994 [DE] Germany .................. 44 46 034.1
Jul. 6, 1995 [DE] Germany .................. 195 24 653.5

[51] Int. Cl.⁶ ...................................... A61F 2/06
[52] U.S. Cl. ........................... 623/1; 623/11; 623/12
[58] Field of Search ................... 623/1–2, 11–12; 606/77–78, 194

[56]           References Cited

U.S. PATENT DOCUMENTS

| | | | |
|---|---|---|---|
| 3,822,238 | 7/1974 | Blair et al. | 260/75 NK |
| 3,975,350 | 8/1976 | Hudgin et al. | 260/30.4 N |
| 4,732,152 | 3/1988 | Wallsten et al. | |
| 5,430,121 | 7/1995 | Pudleiner et al. | 528/28 |
| 5,540,713 | 7/1996 | Schnepp-Pesch et al. | 623/1 |

FOREIGN PATENT DOCUMENTS

| | | |
|---|---|---|
| 0138372 | 10/1982 | European Pat. Off. . |
| 0177330 | 6/1991 | European Pat. Off. . |
| 0587197 | 10/1991 | European Pat. Off. . |
| 9116881 | 10/1991 | Germany . |

Primary Examiner—P. Zuttarelli
Attorney, Agent, or Firm—Friedrich Kueffner

[57]            ABSTRACT

A stent for placement in a body tube includes a flexible support structure composed of an elastomer which is hard in a temperature range lower than 25° C. and soft in a temperature range greater 35° C. The flexible support structure may be embedded in a hollow cylindrical casing of an elastic synthetic material which has a limited elasticity at least at body temperature, wherein the casing is composed of an elastomer which is hard in a temperature range lower than 25° C. and soft in a temperature range greater than 35° C. The casing in which the flexible support structure is embedded may also be of a memory elastomer, particularly on the basis of polyurethane.

5 Claims, 3 Drawing Sheets

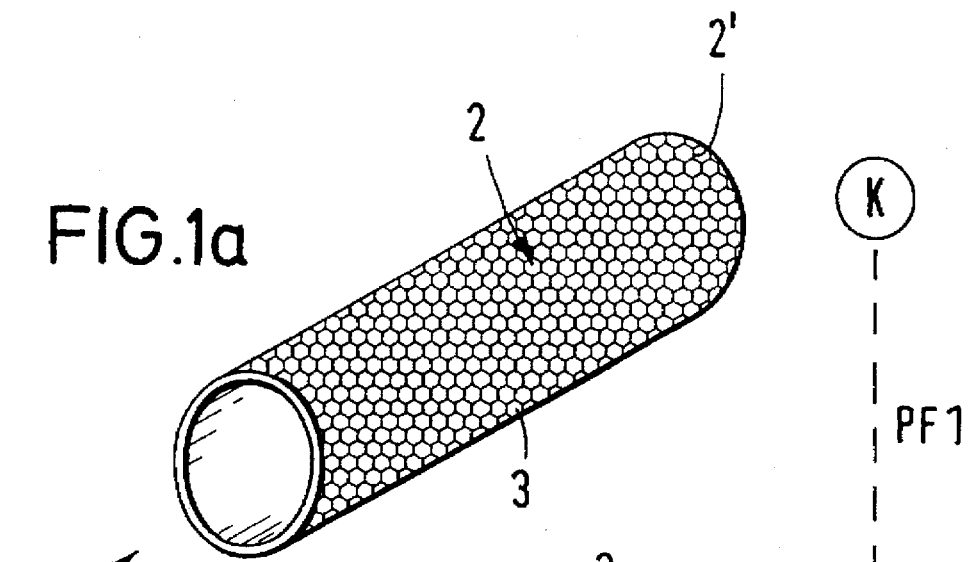
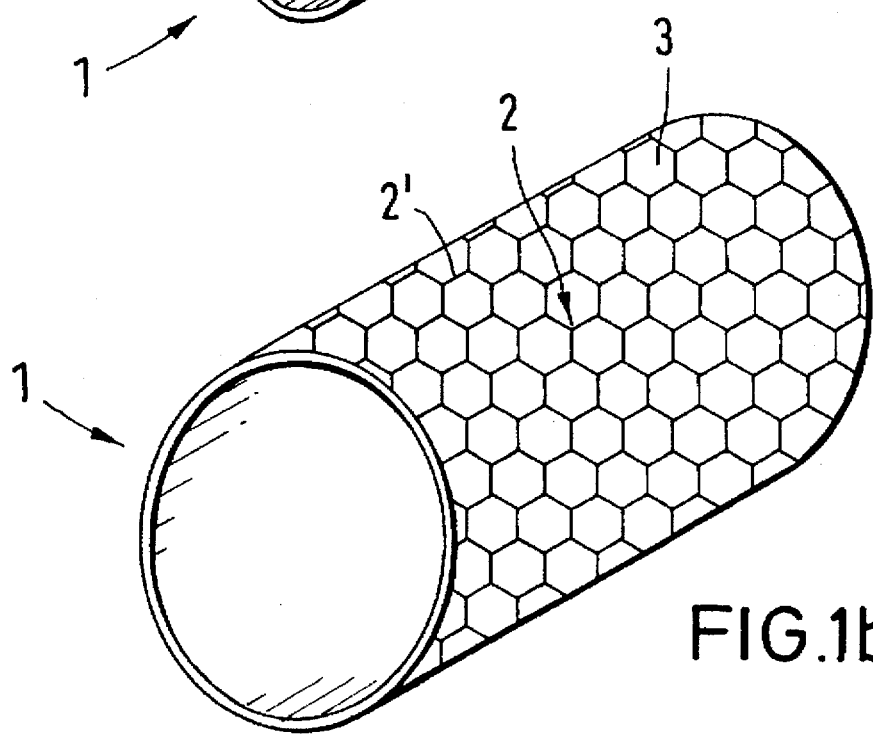

STENT FOR PLACEMENT IN A BODY TUBE

BACKGROUND OF THE INVENTION

1. Field of the Invention

The present invention relates to a stent for placement in a body tube including a flexible support structure.

2. Description of the Related Art

Stents of this type are used in the treatment of stenoses. A stenosis is a congenital or acquired constriction in a body tube. It may occur in hollow organs, such as, trachea, esophagus or also blood vessels and may occur as a result of illness. Depending on the extent of the stenosis, the stenosis causes a partial blocking of the effected body tube or may even entirely close the body tube.

It is known to place so-called stents for expanding or keeping open stenoses, either in blood vessels or other hollow organs. The stents are usually implanted by means of a catheter. Following the implantation, the small internal diameter required for the insertion is changed to a larger internal diameter corresponding to the position of use. The stents keep the vessel open as an internal support and, thus, act as spacer members.

Stents for keeping stenoses open are known in various embodiments. Stents are available in metal and/or synthetic material. They are usually composed of a braided member of metal wires which automatically expand as a result of their natural tension. Self-expanding stents are described, for example, in EP-A-0 183 372 and U.S. Pat. No. 4,732,152. Prior to implantation, these stents are compressed against their natural restoring forces to a reduced cross-section and are inserted by means of a catheter into the body of a patient. After placement in a body tube, the stents expand as a result of their natural tension and are fixed in place as a result.

EP-A 0 177 330 describes a device for implanting a stent, in which a stent compressed to a reduced cross-section is inserted by means of a catheter in a body tube and is then expelled from the catheter.

However, there are also other types of stents which must be expanded into the expanded position in the place of use by means of a suitable device, for example, a balloon catheter.

EP-A 0 587 197 and DE-GM 91 16 881 disclose stents in which the supporting metal segments are embedded in a closed casing of base materials which are compatible with tissue, such as, silicone, in order to prevent growth of tissue cells through the stent.

Also known are stents with metal wires which are composed of a so-called shape memory alloy or memory metal. These stents have a small radial diameter at a low temperature. They are placed in the stenosis in this state. They expand radially when a limiting temperature which is below body temperature is exceeded, so that they can hold a stenosis open in this manner.

The above-described embodiments of stents all have the disadvantage that the procedure for inserting them is complicated. On the one hand, the stent may be bent during insertion because of its flexibility and may get stuck; on the other hand, sometimes complicated insertion instruments are required which surround the stent from the outside and must release the stent at the location of its placement.

Moreover, it is considered a disadvantage that stents are elongated when they are compressed and become shorter again when the pressure is released. This results in problems when planning the treatment of a stenosis because the length of the stent must be adjusted exactly. However, it is also possible that relative movements occur in the body tube between the stent and the vessel wall.

SUMMARY OF THE INVENTION

Therefore, it is the primary object of the present invention to provide a stent of the above-described type which is improved with respect to its configuration as well as to its properties, wherein this stent can be placed in the body in a manner which is better, simpler and gentler.

In accordance with the present invention, the support structure of the stent is composed of an elastomer which is hard in a temperature range lower than 25° C. and is soft in a temperature range greater 35° C.

Accordingly, the present invention utilizes an elastomer for the manufacture of the support structure which is hard at room temperature but is soft at body temperature. Such a temperature-sensitive elastomer has the stiffness required for placing the stent, while, on the other hand, the stent can move similar to tissue after having been placed in the body tube.

The elastomer must always be hard at a temperature of 22° C. The transition from the hard state to the soft state takes place in a temperature range of 25° C. to 35° C. From the medical and surgical perspective, particularly advantageous is an elastomer in which the transition from the essentially hard state to the essentially soft state takes place in a temperature range of 33° C. to 34° C.

In accordance with another feature of the present invention, the stent may be manufactured from one or more threads in a braiding procedure, weaving procedure or knitting procedure. The threads advantageously are composed of a temperature-sensitive polyurethane having the above-described properties. Such a stent provides essentially the three following additional advantages.

First, it is ensured that moisture can penetrate through the support structure. Consequently, the moisture film is built up within the stent, i.e., at the inner diameter of the stent. The moisture film is formed by the moisture transfer from the outer mucous membrane as a result of a type of passive diffusion. Accordingly, a lubricating film always exists at the inner wall surface of the stent.

In addition, the mesh size of the support structure can be varied in accordance with the respective requirements. It is a particular advantage that the mesh size can be adjusted in such a way that a desired tissue formation is facilitated. For example, in a bronchial system, this refers to the growth of functioning ciliated epithelium through the stent. On the other hand, malignant tissue cells are held back.

A further advantage concerns the behavior of the stent with respect to bending and stability. As a result of the hollow cylindrical, braided configuration with inherent stability, the support structure or the stent has such a flexibility that it can be easily guided around curvatures in vessels or the internal diameter of body tubes. Consequently, the stent is distinguished by its non-buckling behavior.

It is basically possible to braid the support structure so tightly that the tissue cells cannot grow through the mesh grid. Consequently, a renewed partial or complete closure of the vessel is avoided.

In accordance with an advantageous embodiment of the present invention, additional threads or strands of a memory metal are arranged in the support structure. The threads or strands are preferably of a nickel/titanium alloy, i.e., the so-called nitinol. This material has a compressed structure at a low temperature. However, the material expands when exceeding a limiting temperature. The desired limiting conditions can be adjusted by the appropriate selection of the alloy components.

At room temperature, the threads of memory metal or nitinol are soft, while the threads of the temperature-sensitive elastomer are hard. The combination of materials results in a stent which is thin and hard at room temperature. At body temperature, the elastomer becomes soft and flexible, while the nitinol expands. As a result, a hard, but elastic stent is obtained which is adjusted in its shape to the internal diameter of the body tube.

The stent can be inserted and placed without problems in a body tube in its thin and hard state. In the case of this stent, an instrument for inserting the stent is not required.

In accordance with another embodiment of the present invention, the stent has a flexible support structure which is embedded in a hollow cylindrical casing of an elastic synthetic material which has a limited elasticity at least at body temperature, wherein the casing is composed of an elastomer which is hard in a temperature range lower than 25° C. and is soft in a temperature range greater than 35° C.

Accordingly, in this embodiment, the flexible support structure is embedded in a hollow cylindrical casing of an elastomer which is hard at room temperature and soft at body temperature.

The casing in which the flexible support structure is embedded may also be of a memory elastomer, particularly on the basis of polyurethane.

Accordingly, the casing of this embodiment is of a temperature-sensitive elastomer, particularly on the basis of polyurethane, which has a shape memory property. In the cold state, this elastomer is hard and small. A stent formed of this material can then be inserted without problems. The memory elastomer, and thus, the stent expands only at body temperature or at a temperature slightly below body temperature.

In accordance with another feature of the present invention, the support structure is formed of metal wires. The support structure my have any desired construction and configuration. The support structure can be woven like a net or may be composed of individual wires which either do not contact each other or are linked together.

The support structure merely must meet the requirement that it permits the expansion process of the casing of memory elastomer. However, this requirement can be met without problems by a suitable configuration of the support structure.

In accordance with another advantageous feature of the invention, the wires of the support structure are of a memory metal, particularly a nickel/titanium alloy, i.e., nitinol. In this embodiment, wires of nitinol are embedded in a casing of memory elastomer. The wires of nitinol are soft at room temperature. On the other hand, the casing is hard. This combination again results in a stent which is thin and hard at room temperature. At body temperature, the memory elastomer becomes soft and flexible, while the support structure of nitinol expands, so that a thick, hard, but elastic stent is obtained.

The insertion procedure and the placement of the thin and hard stent can be carried out simply and precisely without a special insertion instrument. A particular advantage during the insertion procedure is the fact that nitinol is deformable in the cold state, i.e., nitinol has plastically soft properties in the cold state.

The stent is manufactured by combining the memory metal in a state in which it is still soft and deformable with the memory elastomer which is already soft. Consequently, the support structure is cast in its narrow small state into the elastomer. It is important that the manufacturing process is carried out in a temperature range in which the two materials to be combined have not yet changed their state.

In accordance with another advantageous embodiment of the present invention, the support structure of the stent is composed of at least two zigzag-shaped wires which extend parallel to the longitudinal axis of the casing of the stent and which are offset relative to each other on the circumference of the casing, wherein each wire has at least three legs and the middle leg includes an acute angle with each of the two adjoining legs.

The support structure formed of several wires which are arranged offset relative to each other is embedded in the casing of memory elastomer. The casing prevents tissue cells from growing through the support structure.

Such a stent has a uniform restoring force at its circumference. The stent is of uncomplicated construction and, thus, can be manufactured easily.

In accordance with another feature which provides stability in longitudinal direction of the stent, the angle between adjoining legs of each wire is smaller than 45°. As a result of this geometric configuration, the length of the stent does not change even when it is pressed together. This is particularly important in the planning of the treatment of a stenosis because the stent can now be adjusted exactly to its required length.

When a pressure is applied radially from the outside on such a stent, the point of connection or bend between two legs is moved in a rotating movement toward the inside. However, the inner end of the leg is moved simultaneously with its bend in the opposite direction. As a result, the movements cancel each other out. The stent remains stable in its total length.

When a force is applied on the stent which acts in a direction perpendicular to the longitudinal axis of the legs, the wires bend through towards the middle. The adjoining wires would then move away relative from each other. However, this is prevented by the fact that the support structure is embedded in the elastic casing.

If a longitudinal stability of the stent is not required or desired, another feature of the present invention provides that each angle between two adjoining legs is greater than or equal to 45° and smaller than or equal to 90°.

In accordance with a preferred embodiment of the invention, wires arranged next to each other on the circumference of the casing engage in each other in a toothing-like manner. This supports the restoring force of the stent on the circumference thereof.

The engagement of adjacent wires ensures an effective cooperation of the support structure with the casing. When a pressure is applied to the stent, the legs move apart relative from each other, so that a tensile stress is produced in the casing which causes the restoring process. Consequently, the tensile force is transformed in the casing into a compressive force. This compressive force acts against the compressive force acting from the outside and, thus, produces a reaction force in the wires.

In order to prevent displacement of the stent according to the invention in the body tube, the casing may be provided with projections, wherein the projections are distributed over the circumference. The projections may be arranged uniformly or irregularly distributed over the circumference. It is conceivable to form the projections by knobs, hooks or tips. However, in accordance with a particularly advantageous feature, the projections may be formed by bending or twisting the wires forming the support structure in such a way that scale-like projections protrude out of the casing. As a result, the stent has a corrugated surface structure. This configuration is gentler for the vessel walls which come into contact with the stent because a constriction of the blood vessels surrounding the vessel walls is avoided.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

BRIEF DESCRIPTION OF THE DRAWING

In the drawing:

FIG. 1a is a perspective view of a stent according to the invention in the contracted state;

FIG. 1b is a perspective view of the stent of FIG. 1 in the expanded state;

DESCRIPTION OF THE PREFERRED EMBODIMENTS

Figure 2A:
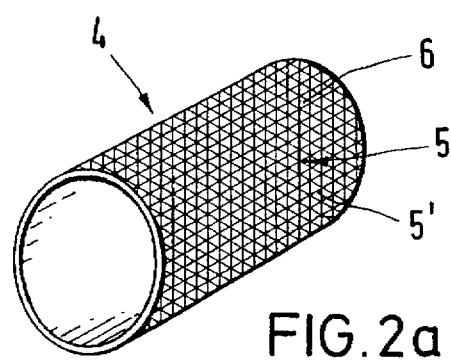
FIGS. 2a is a perspective view of another embodiment of the stent with a casing of memory elastomer.

FIGS. 1a and 1b of the drawing show a stent 1 with a support structure 2 of a shape memory alloy and a casing 3 of a memory elastomer wherein the support structure 2 is embedded in the casing 3. The support structure 2 is woven of wires 2'.

FIG. 1a shows the stent 1 in the cold state K. In this phase, the casing 3 of memory elastomer is hard and small. The support structure 2 is also small, but deformable, because the memory metal has plastically soft properties.

In this state, the stent 1 can be easily inserted into a body tube affected by a stenosis.

An expansion of the stent 1 only occurs at a temperature which is slightly below body temperature. The stent 1 then is transposed into the state W which is illustrated in FIG. 1b. The transition of the stent 1 from the state K to the state W is indicated by an arrow PF1 for the temperature pattern.

In the state W, the casing 3 is soft and flexible; the support structure 2 has expanded. The stent 1 is now hard, but elastic. The stent 1 completely fills out the internal diameter of the affected body tube and is capable of supporting the body tube.

FIG. 2a shows a stent 4 whose support structure 5 of nitinol wires 5' has a net-like structure. The support structure 5 is also embedded in a casing 6 of memory elastomer.

Figure 2B:
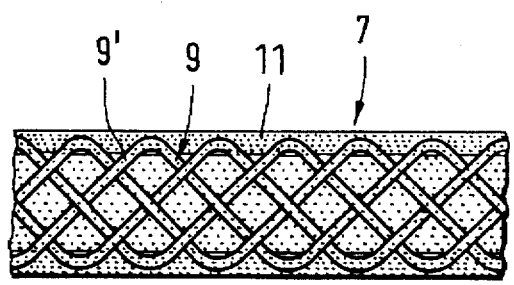
FIGS. 2b and 2c are side views of additional embodiments of stents with casings of memory elastomer.
Figure 2C:
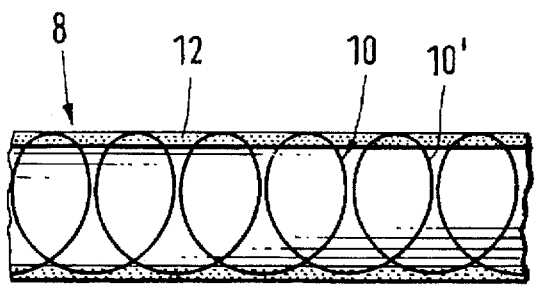

FIGS. 2b and 2c are partial views of stents 7 and 8, respectively. The stents 7 and 8 are essentially of the same configuration as stent 4. Stents 7 and 8 each have a support structure 9, 10 of memory metal wires 9' and 10', respectively, wherein the support structure is embedded in a casing 11 or 12, respectively, of a memory elastomer.

Figure 3:
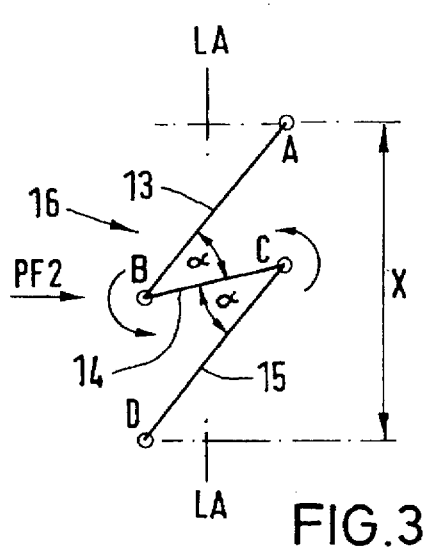
FIG. 3 is a side view of a support wire with three legs, showing the sequence of movements of the wire.

FIG. 3 shows a support wire 16 with three legs 13, 14, 15. The middle leg 14 includes with each of the two adjoining legs 13 and 15 an acute angle α. The end or bending points between the legs are denoted by letters A through D.

The points A and D characterize two points located at the outer ends of the stent and are to be considered fixed. When a radial pressure is applied against the tip B from the outside in accordance with arrow PF2, the tip B moves in a rotating movement in the plane of the drawing toward the bottom and toward the inside. Simultaneously, the inner tip C moves in an opposite movement toward the outside and up. The movements are superimposed and cancel each other out. Consequently, the total length X of the support wire 16 remains constant. The end points A and D remain stationary.

When a force directed perpendicularly into the plane of the drawing acts on the wire 16, the wire 16 will be bent perpendicularly to its longitudinal axis LA.

Consequently, a stent whose support structure is composed of support wires in accordance with the configuration of support wire 16, remains stable in its total length, even when it is compressed.

Figure 4:
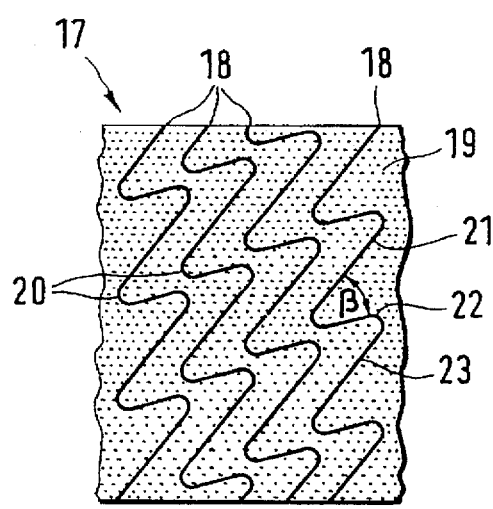
FIG. 4 is a developed view of a stent.

FIG. 4 of the drawing shows a portion of a stent 17. The support wires 18 of memory metal are again surrounded by a casing 19 of memory elastomer.

The individual wires 18 engage in each other in a toothing-like manner with the rounded length portions 20. The individual legs 21, 22, 23 include acute angles β with each other. Consequently, the middle leg 22 is shorter than the two adjoining legs 21 and 23.

Figure 5:
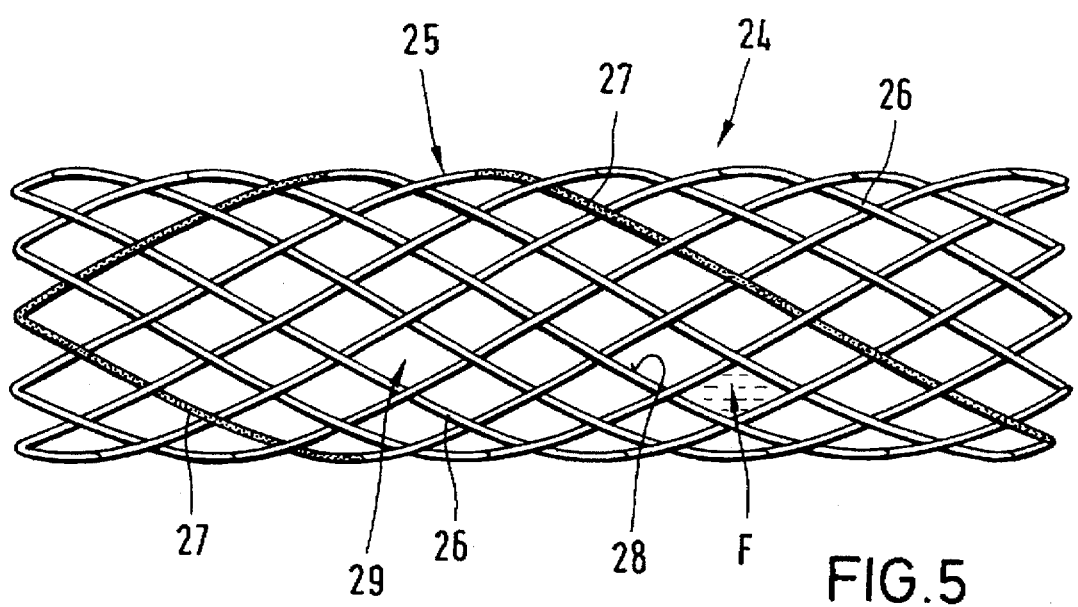
FIG. 5 is a side view, on a larger scale, of a stent having a braided support structure.

FIG. 5 shows a stent 24 in which the support structure 25 is manufactured by braiding individual threads 26 and 27. The threads 26 are of a temperature-sensitive polyurethane, while the threads 27 are of nitinol.

At a temperature below 25° C., the threads 26 are hard and small. In this temperature range the threads 27 are compressed, i.e., they are in a contracted state. When reaching the limiting temperature of 34° C., the threads 26 become soft and elastic, and the threads 27 expand.

In a stent 24 which has been inserted in a body vessel, moisture can pass from the outer mucous membrane of the body vessel into the interior area of the stent 24. Consequently, a moisture film F is formed on the inner wall 28 of the stent.

Because of its round braided configuration, the stent 24 is additionally distinguished by its positive properties with respect to bending and stability. Buckling of the cylindrical configuration at body tube curvatures is essentially avoided.

The size of the meshes 29 in the stent 24 is selected in such a way that tissue which is capable of functioning can grow through the meshes.

While specific embodiments of the invention have been shown and described in detail to illustrate the inventive principles, it will be understood that the invention may be embodied otherwise without departing from such principles.

I claim:

1. A stent for placement in a body tube, the stent comprising a flexible support structure, wherein the support structure is of an elastomer which has a high stiffness in a temperature range lower than 25° C. and is soft so as to be flexible such that the structure can be easily guided around curvatures of the body tube in a temperature range higher than 35° C., wherein the support structure has meshes, the meshes having a size selected such that tissue capable of functioning can grow through the meshes.

2. The stent according to claim 1, wherein the support structure comprises at least one thread, the at least one thread being braided for stabilizing the support structure.

3. The stent according to claim 1, wherein the support structure comprises threads, the threads being braided for stabilizing the support structure.

4. The stent according to claim 3, further comprising at least one additional thread of a memory metal.

5. The stent according to claim 4, wherein the thread is of a nickel/titanium alloy.

* * * * *